United States Patent
Touchi

(10) Patent No.: US 11,534,629 B2
(45) Date of Patent: Dec. 27, 2022

(54) PARTICLE BEAM APPARATUS

(71) Applicant: SUMITOMO HEAVY INDUSTRIES, LTD., Tokyo (JP)

(72) Inventor: Yutaka Touchi, Ehime (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 17/204,192

(22) Filed: Mar. 17, 2021

(65) Prior Publication Data
US 2021/0290983 A1 Sep. 23, 2021

(30) Foreign Application Priority Data
Mar. 18, 2020 (JP) .............................. JP2020-047850

(51) Int. Cl.
- *H05H 7/04* (2006.01)
- *A61N 5/10* (2006.01)
- *G01R 33/36* (2006.01)
- *G01R 33/381* (2006.01)

(52) U.S. Cl.
CPC ............ *A61N 5/1077* (2013.01); *G01R 33/36* (2013.01); *G01R 33/381* (2013.01); *H05H 7/04* (2013.01); *A61N 2005/1087* (2013.01)

(58) Field of Classification Search
CPC .. A61N 5/1077; A61N 5/1078; A61N 5/1079; H05H 7/04; H05H 2007/045; H05H 2007/046

See application file for complete search history.

(56) References Cited

U.S. PATENT DOCUMENTS

2020/0330793 A1* 10/2020 Aoki ..................... H05H 13/02

FOREIGN PATENT DOCUMENTS

EP 3020452 A1 * 5/2016 .......... A61N 5/1048

OTHER PUBLICATIONS

G. Balbinot et al., "Beam Diagnostics in the Cnao Injection Lines Commissioning", Proceedings of DIPAC09, Basel, Switzerland, Jan. 2009, pp. 119-121, Paper ID: MOPD31, 01 Overview and Commissioning.

Tim Winkelmann et al., "Long-Term Operation Experience With Two ECR Ion Sources and Planned Extensions At Hit", Proceedings of ECRIS2010, Grenoble, France, Jan. 2008, pp. 153-155, Paper ID: TUPOT016, 10 Applications.

T. Winkelmann et al., "Integration of a Third Ion Source for Heavy Ion Radiotherapy At Hit", Proceedings of ECRIS2012, Sydney, Australia, 2012, ISBN 978-3-95450-123-6, pp. 46-48, Paper ID: TUPP03, Applications.

* cited by examiner

Primary Examiner — Eliza W Osenbaugh-Stewart
(74) Attorney, Agent, or Firm — Michael Best & Friedrich LLP

(57) ABSTRACT

A particle beam apparatus includes: an electromagnet to which each ion beam from a plurality of ion sources having different ion species is capable of being introduced, and from which one of the ion beams is capable of selectively exiting to a device on a downstream side by switching a magnetic field intensity, in which the electromagnet is capable of deflecting the one of the ion beam to be exited to the device on the downstream side toward the device on the downstream side, and is capable of reducing exit of a different type of beam mixed in the ion beam to the device on the downstream side, the different type of beam being different from the one of the ion beam.

12 Claims, 3 Drawing Sheets

PARTICLE BEAM APPARATUS

RELATED APPLICATIONS

The content of Japanese Patent Application No. 2020-047850, on the basis of which priority benefits are claimed in an accompanying application data sheet, is in its entirety incorporated herein by reference.

BACKGROUND

Technical Field

Certain embodiments of the present invention relate to a particle beam apparatus.

Description of Related Art

As a particle beam apparatus, for example, a particle beam apparatus of the related art is known. The particle beam apparatus is provided with two ion sources so as to be able to supply two types of ion beams to a beam acceleration unit. Two beam transport paths from the respective ion sources are merged at an electromagnet, a beam transport path further extends from the electromagnet to the downstream side, and the beam acceleration unit is disposed at a downstream end of the beam transport path. A bending electromagnet exists on the beam transport path between each ion source and the electromagnet, and the ion beam from the ion source is deflected by about 90° by the bending electromagnet and transported to the electromagnet at a merging part.

SUMMARY

According to an embodiment of the present invention, there is provided According to an embodiment of the present invention, there is provided a particle beam apparatus including an electromagnet to which each ion beam from a plurality of ion sources having different ion species is capable of being introduced, and from which one of the ion beams is capable of selectively exiting to a device on a downstream side by switching a magnetic field intensity, in which the electromagnet is capable of deflecting the one of the ion beam to be exited to the device on the downstream side toward the device on the downstream side, and is capable of reducing exit of a different type of beam mixed in the ion beam to the device on the downstream side, the different type of beam being different from the one of the ion beam.

DETAILED DESCRIPTION

In facilities where this type of particle beam apparatus is installed, in many cases, installation space is limited, and therefore, downsizing of the particle beam apparatus has been desired. Further, a reduction in the cost of this type of particle beam apparatus has also been desired. It is desirable to provide a particle beam apparatus in which it is possible to achieve downsizing and a reduction in cost.

The particle beam apparatus according to the embodiment of the present invention may further include a current measuring device into which one of the ion beams introduced into the electromagnet is incident, and which is capable of measuring a beam current of the ion beam, in which one of the ion beams different from the ion beam that is directed to the device on the downstream side may be incident into the current measuring device. Further, the current measuring device maybe installed in the interior of the electromagnet.

According to the present invention, it is possible to provide a particle beam apparatus in which it is possible to achieve downsizing and a reduction in cost.

Hereinafter, a particle beam apparatus 1 according to the present invention will be described in detail with reference to the drawings. In the following, an XYZ Cartesian coordinate system is set as shown in each of the drawings, and there is a case where X, Y, and Z are used to describe the positional relationship of each part.

Figure 1:
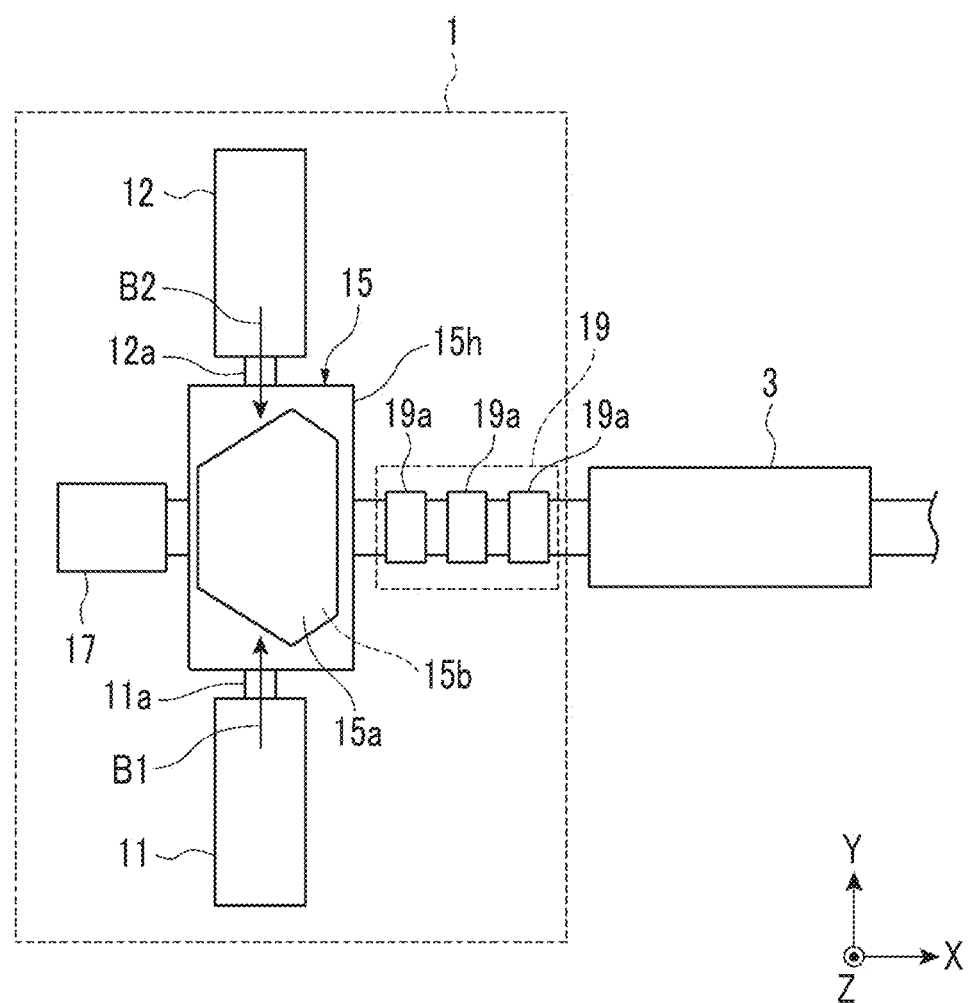
FIG. 1 is a plan view showing a particle beam apparatus.

The particle beam apparatus 1 shown in FIG. 1 is an apparatus that is used in, for example, a particle beam therapy apparatus and supplies an ion beam to a beam acceleration unit 3 of the particle beam therapy apparatus. The beam acceleration unit 3 is, for example, a linear accelerator such as an RFQ (radio-frequency quadrupole). The ion beam supplied from the particle beam apparatus 1 and accelerated by the beam acceleration unit 3 is transported to a main body part (not shown) of the particle beam therapy apparatus. In the main body part, particle beam therapy is performed by irradiating a patient to be treated with the ion beam. The particle beam apparatus 1 includes two ion sources such as a first ion source 11 and a second ion source 12, a bending electromagnet 15, a beam diagnostic device 17 (a current measuring device), and a beam transport system (LEBT: Low Energy Beam Transport) 19.

The first ion source 11 and the second ion source 12 are devices for generating ions, and are, for example, ECR ion sources. The first ion source 11 and the second ion source 12 generate ions different from each other. In the present embodiment, it is assumed that positive and negative charges of the ion that is generated by the first ion source 11 and the ion that is generated by the second ion source 12 are the same. In the present embodiment, a case where the first ion source 11 generates $C^{4+}$ and the second ion source 12 generates $He^{2+}$ ($\alpha$ particles) will be described as an example.

As shown in FIG. 1, the first ion source 11, the bending electromagnet 15, and the second ion source 12 are arranged in a Y direction in this order, that is, the bending electromagnet 15 is disposed to be interposed between the first ion source 11 and the second ion source 12 in the Y direction. The first ion source 11 and the second ion source 12 emit ion beams in directions facing each other, and each ion beam is introduced into the bending electromagnet 15. Specifically, the first ion source 11 emits an ion beam B1 (hereinafter referred to as a "first ion beam B1") in a +Y direction, and the first ion beam B1 is incident into the bending electromagnet 15. Further, the second ion source 12 emits an ion beam B2 (hereinafter referred to as a "second ion beam B2") in a −Y direction, and the second ion beam B2 is incident into the bending electromagnet 15. Here, the first ion source 11 and the second ion source 12 are operated at the same time, and both the first ion beam B1 and the second ion beam B2 are simultaneously incident into the bending electromagnet 15.

It is not necessary to provide a beam converging device that converges the first ion beam B1 by a magnetic field between the first ion source 11 and the bending electromagnet 15. Therefore, a beam exit nozzle 11a of the first ion source 11 is directly connected to a casing 15h of the bending electromagnet 15. Similarly, it is not necessary to provide a beam converging device that converges the second ion beam B2 by a magnetic field between the second ion source 12 and the bending electromagnet 15, and a beam exit nozzle 12a of the second ion source 12 is directly connected to the casing 15h of the bending electromagnet 15.

The bending electromagnet 15 includes a pair of magnetic poles 15a and 15b facing each other at an interval in a Z direction, and the casing 15h that accommodates the magnetic poles 15a and 15b and has an evacuated inside. In the bending electromagnet 15, an electric current is supplied to a coil (not shown) of the magnetic pole 15a and a coil (not shown) of the magnetic pole 15b, whereby a magnetic field is formed in a gap between the magnetic pole 15a and the magnetic pole 15b. The first ion beam B1 and the second ion beam B2 are introduced into the gap between the magnetic pole 15a and the magnetic pole 15b, and are deflected bypassing through the above magnetic field. The magnetic field intensity of the bending electromagnet 15 (the magnetic field intensity between the magnetic pole 15a and the magnetic pole 15b) is appropriately adjusted, whereby a state is created where one of the first ion beam B1 and the second ion beam B2 is deflected toward the beam transport system 19 that is a device on the downstream side and the other is deflected toward the beam diagnostic device 17 (refer to FIGS. 2A and 2B).

Figure 2A:
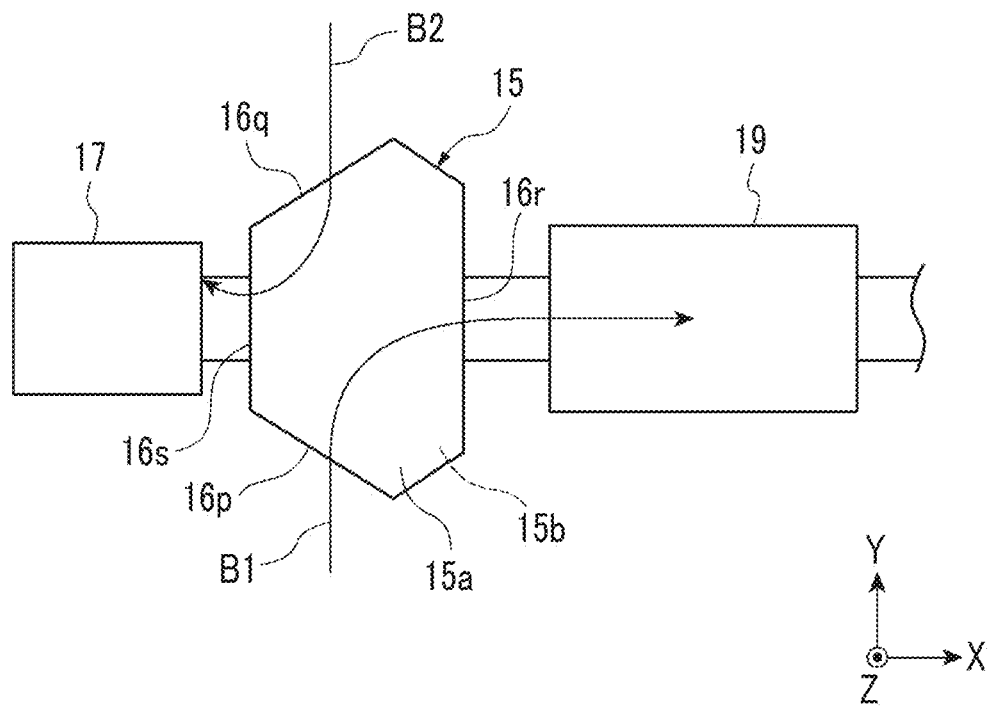
FIG. 2A is a diagram schematically showing the vicinity of a bending electromagnet in a first state.
Figure 2B:
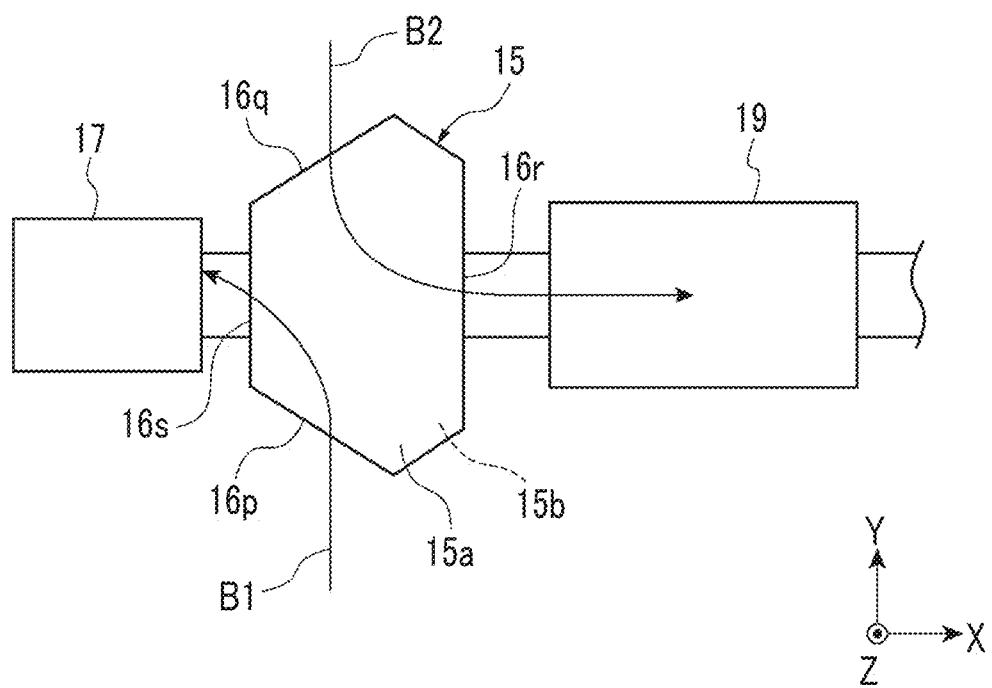
FIG. 2B is a diagram schematically showing the vicinity of the bending electromagnet in a second state.

As shown in FIGS. 2A and 2B, the magnetic poles 15a and 15b of the bending electromagnet 15 have the same shape and overlap each other in the Z direction. Each of the magnetic poles 15a and 15b has a hexagonal shape when viewed from the Z direction, and has edges 16p, 16q, 16r, and 16s corresponding to four sides among six sides of the hexagonal shape. The first ion beam B1 is introduced into the bending electromagnet 15 across the edge 16p, and the second ion beam B2 is introduced into the bending electromagnet 15 across the edge 16q. Further, one of the first ion beam B1 and the second ion beam B2 deflected toward the beam transport system 19 exits from the bending electromagnet 15 across the edge 16r, and the other deflected toward the beam diagnostic device 17 exits from the bending electromagnet 15 across the edge 16s. The edges 16r and 16s are edges extending in the Y direction. The edge 16p is inclined with respect to an X direction, and the first ion beam B1 that is introduced into the bending electromagnet 15 diagonally crosses the edge 16p. Similarly, the edge 16q is also inclined with respect to the X direction, and the second ion beam B2 that is introduced into the bending electromagnet 15 diagonally crosses the edge 16q. In this manner, the first ion beam B1 and the second ion beam B2 diagonally cross the edges 16p and 16q of the bending electromagnet 15, whereby the first ion beam B1 and the second ion beam B2 are converged.

As shown in FIG. 1, the beam diagnostic device 17, the bending electromagnet 15, and the beam transport system 19 are arranged in the X direction in this order, that is, the bending electromagnet 15 is disposed to be interposed between the beam diagnostic device 17 and the beam transport system 19 in the X direction. The beam transport system 19 transports an ion beam (one of the first ion beam B1 and the second ion beam B2) exited from the bending electromagnet 15 in a +X direction to the beam acceleration unit 3. The beam transport system 19 is configured to include three electrostatic quadrupole electromagnets 19a that converge the ion beam.

An ion beam (the other of the first ion beam B1 and the second ion beam B2) exited from the bending electromagnet 15 in a −X direction is incident into the beam diagnostic device 17, and a beam current of the ion beam is measured by the beam diagnostic device 17. The beam diagnostic device 17 maybe capable of further measuring a beam profile of the ion beam.

In the particle beam apparatus 1 having the configuration described above, a desired ion beam of the first ion beam B1 and the second ion beam B2 can be selectively supplied to the beam acceleration unit 3 and used for the particle beam therapy. In this manner, a mechanism for switching between the state of the particle beam apparatus 1 that supplies the first ion beam B1 to the beam acceleration unit 3 (hereinafter referred to as a "first state") and the state of the particle beam apparatus 1 that supplies the second ion beam B2 (hereinafter referred to as a "second state") will be described below. FIG. 2A is a diagram schematically showing the vicinity of the bending electromagnet 15 in the first state of the particle beam apparatus 1, and FIG. 2B is a diagram schematically showing the vicinity of the bending electromagnet 15 in the second state of the particle beam apparatus 1.

First State

As shown in FIG. 2A, in the first state, the first ion beam B1 exits from the beam exit nozzle 11a of the first ion source 11 in the +Y direction and is introduced into the bending electromagnet 15. Then, the first ion beam B1 is bent by receiving the Lorentz force in the direction orthogonal to an advancing direction due to the magnetic field of the bending electromagnet 15, and finally exits from the bending electromagnet 15 in the +X direction to exit to the beam transport system 19 (a deflection function of the bending electromagnet 15).

Since a bending direction or curvature of the first ion beam B1 as described above depends on the magnetic field intensity of the bending electromagnet 15 (the magnetic field intensity between the magnetic pole 15a and the magnetic pole 15b), the magnetic field intensity of the bending electromagnet 15 is appropriately set, whereby the first ion beam B1 can be exited to the beam transport system 19. That is, it is favorable if the magnetic field intensity is set such that the first ion beam B1 ($C^{4+}$ beam) is deflected by 90° toward the beam transport system 19 side in the bending electromagnet 15. The first ion beam B1 incident into the beam transport system 19 passes through the beam acceleration unit 3 and is used for the particle beam therapy, as described above.

On the other hand, in the first state, the second ion beam B2 exits from the beam exit nozzle 12a of the second ion source 12 in the −Y direction and is introduced into the bending electromagnet 15. Then, the second ion beam B2 is bent by receiving the Lorentz force in the direction orthogonal to the advancing direction due to the magnetic field of the bending electromagnet 15, and finally exits from the bending electromagnet 15 in the −X direction to exit to the beam diagnostic device 17. In the beam diagnostic device 17, a beam current of the second ion beam B2 is measured.

Second State

As shown in FIG. 2B, in the second state, the Lorentz force opposite to that in the first state acts on the first ion beam B1 and the second ion beam B2, so that the second ion beam B2 is exited to the beam transport system 19 and the first ion beam B1 is exited to the beam diagnostic device 17. The second ion beam B2 incident into the beam transport system 19 passes through the beam acceleration unit 3 and is used for the particle beam therapy, as described above, and in the beam diagnostic device 17, a beam current of the first ion beam B1 is measured. In order to realize such a second state, it is favorable if the magnetic field intensity of the bending electromagnet 15 is set such that the second ion beam B2 ($He^{2+}$ beam) is deflected by 90° toward the beam transport system 19 side in the bending electromagnet 15.

Switching Between First State and Second State

The switching between the first state and the second state as described above can be executed by switching the magnetic field intensity of the bending electromagnet 15. This switching of the magnetic field intensity also includes reversal of the polarities of the magnetic poles 15a and 15b. Such switching of the magnetic field intensity of the bending electromagnet 15 is specifically realized by switching a supply current to the coil (not shown) of the magnetic pole 15a and the coil (not shown) of the magnetic pole 15b.

Analysis Function of Bending Electromagnet 15

The bending electromagnet 15 has an analysis function, in addition to the deflection function as described above. The analysis function is a function of reducing the exit of different types of beams mixed in the ion beam to be sent to the beam transport system 19 to the beam transport system 19. For example, in the first ion source 11, in addition to the required $C^{4+}$ beam, different types of beams such as a $C^{2+}$ beam, a $C^{3+}$ beam, a $C^{5+}$ beam, a nitrogen ion beam, an oxygen ion beam, and a hydrogen ion beam are also generated together, and these are introduced into the bending electromagnet 15 together with the $C^{4+}$ beam.

In the first state, as described above, the magnetic field intensity of the bending electromagnet 15 is set such that the $C^{4+}$ beam is deflected by 90° toward the beam transport system 19 side. In this magnetic field intensity, the different types of beams as described above bend with curvature different from that of the $C^{4+}$ beam due to a difference in mass or charge, so that the beams hardly exit to the beam transport system 19 due to collision with the casing 15h or the like of the bending electromagnet 15, or the like. The bending electromagnet 15 exhibits such an analysis function, whereby the different types of beams that are sent to the beam acceleration unit 3 are reduced. Further, the bending electromagnet 15 exhibits the analysis function, whereby it is not necessary to separately install a device having an analysis function (for example, another bending electromagnet) between the first ion source 11 and the bending electromagnet 15, and the first ion source 11 and the bending electromagnet 15 can be directly connected.

Here, the analysis function that is exhibited in the first state has been described as an example. However, the same applies to the analysis function that is exhibited in the second state. That is, in the second ion source 12, in addition to the required $He^{2+}$ beam, different types of beams such as a nitrogen ion beam, an oxygen ion beam, and a hydrogen ion beam are also generated together, and in the second state, when these different types of beams are introduced into the bending electromagnet 15 together with the $He^{2+}$ beam, the analysis function of the bending electromagnet 15 is exhibited in the same manner as described above, so that the different types of beams that are sent to the beam acceleration unit 3 are reduced.

Further, in the first state, the magnetic field intensity of the bending electromagnet 15 deflects the first ion beam B1 ($C^{4+}$ beam) by 90°, and therefore, at this magnetic field intensity, the deflection of the second ion beam B2 ($He^{2+}$ beam) is different from 90°. Therefore, in the first state, the second ion beam B2 is not completely incident into the central position of the beam diagnostic device 17 in the −X direction. For the same reason, in the second state, the first ion beam B1 is not completely incident into the central position of the beam diagnostic device 17 in the −X direction. That is, the incident positions of the second ion beam B2 in the first state and the first ion beam B1 in the second state into the beam diagnostic device 17 are different from each other in the Y direction. Therefore, a Y direction dimension of a beam incident port of the beam diagnostic device 17 is set such that both the second ion beam B2 in the first state and the first ion beam B1 in the second state are incident into the beam diagnostic device 17.

Figure 3:
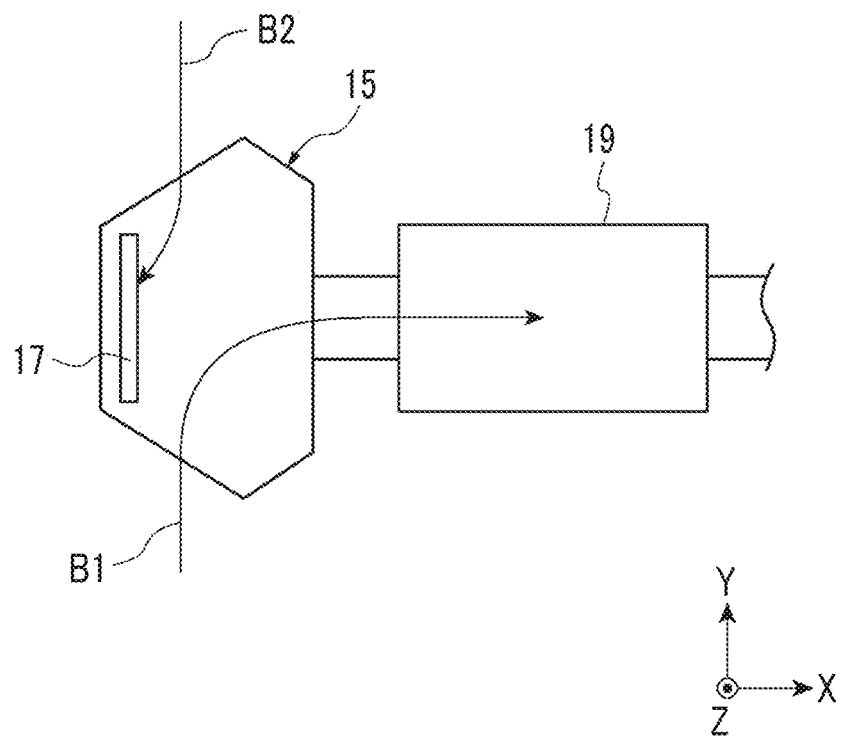
FIG. 3 is a diagram schematically showing the vicinity of a bending electromagnet of a particle beam apparatus according to a modification example.

As another configuration for causing both the second ion beam B2 in the first state and the first ion beam B1 in the second state to be incident into the beam diagnostic device 17, as shown in FIG. 3, the beam diagnostic device 17 maybe installed in the interior of the bending electromagnet 15. The beam diagnostic device 17 in this case is located to be interposed between the magnetic pole 15a and the magnetic pole 15b in the Z direction. In this case, the Y direction dimension of the beam incident port of the beam diagnostic device 17 can be reduced as compared with the configuration in FIGS. 2A and 2B.

Subsequently, the operation and effects of the particle beam apparatus 1 will be described.

In the particle beam apparatus 1, the respective ion beams (the first ion beam B1 and the second ion beam B2) can be introduced into the bending electromagnet 15 from a plurality of ion sources (the first ion source 11 and the second ion source 12). Then, any one of the plurality of ion beams (the first ion beam B1 or the second ion beam B2) is selectively exited to the beam transport system 19 by switching the magnetic field density of the bending electromagnet 15. At this time, the bending electromagnet 15 exhibits the deflection function of deflecting the ion beam to exit to the beam transport system 19 toward the beam transport system 19. Further, the bending electromagnet 15 exhibits the analysis function of reducing the exit of the different types of beams mixed in the ion beam to exit to the beam transport system 19 to the beam transport system 19.

Since a plurality of ion beams having different ion species can be switched and sent to the beam transport system 19 by switching the magnetic field density of the bending electromagnet 15, components on the downstream side of the beam from the beam transport system 19 can be shared, and a plurality of types of ion beams can be used for the particle beam therapy while being selectively switched. Further, the switching of the ion beam as described above can be executed in a short time by switching the magnetic field density of the bending electromagnet 15. Further, since the bending electromagnet 15 exhibits the analysis function, different types of beams that are sent to the downstream side through the beam transport system 19 are reduced. Further, the bending electromagnet 15 exhibits the analysis function, whereby it is not necessary to separately install a device (for example, another bending electromagnet) having an analysis function between the first ion source 11 and the bending electromagnet 15 and between the second ion source 12 and the bending electromagnet 15. Then, the particle beam apparatus 1 can be downsized by directly connecting the first ion source 11 and the bending electromagnet 15 and directly connecting the second ion source 12 and the bending electromagnet 15. Further, a device between the first ion source 11 and the bending electromagnet 15 and a device between the second ion source 12 and the bending electromagnet 15 are omitted, so that the cost of the particle beam apparatus 1 can be reduced.

Further, the ion sources (the first ion source 11 and the second ion source 12) and the bending electromagnet 15 are directly connected, so that a beam transport route from each ion source to the bending electromagnet 15 is shortened. Then, the diffusion of the ion beams (the first ion beam B1 and the second ion beam B2) from the ion sources to the bending electromagnet 15 is reduced, and therefore, it is possible to reduce the number of beam converging magnets that need to be installed on the beam transport route, and thus the cost of the particle beam apparatus 1 can be reduced.

Further, an ion beam different from the ion beam that is used for the particle beam therapy is incident into the beam diagnostic device 17, and thus it is possible to obtain information such as the beam current of the ion beam. In this manner, the beam current or the like can be measured when the ion beam is not used for the particle beam therapy. Then, in order to obtain information such as the beam current, for example, a mechanical drive mechanism or the like for inserting and removing a beam diagnostic device may be constructed on the trajectory of the ion beam. However, the cost of the particle beam apparatus 1 may be reduced by omitting the mechanical drive mechanism or the like.

The present invention can be implemented in various forms having various modifications and improvements made based on the knowledge of those skilled in the art, including the embodiment described above. Further, it is possible to configure a modification example of the example by utilizing the technical matters described in the embodiment described above. The configurations of the respective embodiments maybe appropriately combined and used.

For example, it is not essential that the particle beam apparatus includes the beam diagnostic device 17, and for example, a beam stopper may be installed in place of the beam diagnostic device 17. Further, in the embodiment, an incident direction of the first ion beam B1 into the bending electromagnet 15 and an incident direction of the second ion beam B2 into the bending electromagnet 15 face each other. However, these incident directions may intersect each other at a predetermined angle. Further, in the embodiment, the first ion source 11 and the second ion source 12 are operated at the same time. However, when one ion source is used for the particle beam therapy, the operation of the other ion source may be stopped.

Further, in the embodiment, there are two ion sources (the first ion source 11 and the second ion source 12) that introduce ion beams into the bending electromagnet 15. However, there may be three or more such ion sources. Further, in the embodiment, the example in which the first ion beam B1 and the second ion beam B2 that are handled by the particle beam apparatus 1 are a $C^{4+}$ beam and a $He^{2+}$ beam has been described. However, there is no limitation thereto, and for example, the first ion beam B1 or the second ion beam B2 may be $H^+$, $H^{2+}$, $He^{2+}$, $C^{4+}$, or the like.

It should be understood that the invention is not limited to the above-described embodiment, but may be modified into various forms on the basis of the spirit of the invention. Additionally, the modifications are included in the scope of the invention.

What is claimed is:

1. A particle beam apparatus comprising:
an electromagnet to which each ion beam from a plurality of ion sources having different ion species is capable of being introduced, and from which one of the ion beams is capable of selectively exiting to a device on a downstream side by switching a magnetic field intensity; and
a current measuring device into which one of the ion beams introduced into the electromagnet is incident, and which is capable of measuring a beam current of the ion beam,
wherein the electromagnet is capable of deflecting the one of the ion beams to be exited to the device on the downstream side toward the device on the downstream side, and is capable of reducing exit of a different type of beam mixed in the ion beam to the device on the downstream side, the different type of beam being different from the one of the ion beams, and
one of the ion beams different from the ion beam that is directed to the device on the downstream side is incident into the current measuring device.

2. The particle beam apparatus according to claim 1,
wherein the plurality of ion sources include a first ion source and a second ion source,
the electromagnet is disposed to be interposed between the first ion source and the second ion source, and
the first ion source and the second ion source respectively emit a first ion beam and a second ion beam in directions facing each other, and the first ion beam and the second ion beam are introduced into the electromagnet.

3. The particle beam apparatus according to claim 2,
wherein a beam exit nozzle of the first ion source and a beam exit nozzle of the second ion source are directly connected to a casing of the electromagnet.

4. The particle beam apparatus according to claim 2,
wherein the electromagnet includes a first magnetic pole and a second magnetic pole having the same shape and facing each other at an interval, and a casing that accommodates the first magnetic pole and the second magnetic pole and has an evacuated inside, and
an electric current is supplied to a coil of the first magnetic pole and a coil of the second magnetic pole, whereby a magnetic field is formed in a gap between the first magnetic pole and the second magnetic pole.

5. The particle beam apparatus according to claim 4,
wherein each of the first magnetic pole and the second magnetic pole has a substantially hexagonal shape when viewed from a direction in which the first magnetic pole and the second magnetic pole face each other, and has four edges corresponding to four sides among six sides of the substantially hexagonal shape, and
the four edges include a first edge inclined with respect to a direction perpendicular to a direction in which the first ion source and the second ion source face each other when viewed from the direction in which the first magnetic pole and the second magnetic pole face each other, a second edge inclined with respect to a direction perpendicular to the direction in which the first ion source and the second ion source face each other when viewed from the direction in which the first magnetic pole and the second magnetic pole face each other, a third edge extending in the direction in which the first ion source and the second ion source face each other, and a fourth edge extending in the direction in which the first ion source and the second ion source face each other.

6. The particle beam apparatus according to claim 5, wherein the first ion beam is introduced into the electromagnet diagonally across the first edge, and the second ion beam is introduced into the electromagnet diagonally across the second edge.

7. The particle beam apparatus according to claim 6, wherein the first ion beam or the second ion beam introduced into the electromagnet exits from the electromagnet across the third edge or the fourth edge.

8. The particle beam apparatus according to claim 1, wherein the electromagnet is disposed to be interposed between the current measuring device and the device on the downstream side.

9. The particle beam apparatus according to claim 1, wherein the current measuring device is installed in an interior of the electromagnet.

10. The particle beam apparatus according to claim 9, wherein the electromagnet includes a first magnetic pole and a second magnetic pole having the same shape and facing each other at an interval, and the current measuring device is disposed to be interposed between the first magnetic pole and the second magnetic pole.

11. The particle beam apparatus according to claim 1, wherein the device on the downstream side is a beam transport system, and transports the ion beam exited from the electromagnet to a beam acceleration unit.

12. The particle beam apparatus according to claim 11, wherein the beam transport system includes three electrostatic quadrupole electromagnets that converge the ion beam.

* * * * *